(12) United States Patent
Tovey

(10) Patent No.: US 6,361,769 B1
(45) Date of Patent: *Mar. 26, 2002

(54) STIMULATION OF HOST DEFENSE MECHANISMS AGAINST VIRAL CHALLENGES

(75) Inventor: Michael Gerard Tovey, Paris (FR)

(73) Assignee: Pharma Pacific Pty Ltd, New South Wales (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/853,292

(22) Filed: May 9, 1997

(51) Int. Cl.$^7$ .......................... A61K 38/21; A61K 38/00
(52) U.S. Cl. .................... 424/85.4; 424/85.1; 424/85.5; 424/85.6; 424/85.7; 514/2
(58) Field of Search ............................... 424/85.4, 85.5, 424/85.6, 85.7, 85.1; 514/2

(56) References Cited

U.S. PATENT DOCUMENTS

| 4,605,555 A | 8/1986 | Sato et al. ..................... 424/85 |
| 4,820,514 A | 4/1989 | Cummins .................. 424/85.4 |
| 4,946,674 A | 8/1990 | von Eichborn et al. |
| 5,019,382 A | 5/1991 | Cummins, Jr. ............. 424/85.4 |
| 5,145,677 A | 9/1992 | von Eichborn et al. |
| 5,215,741 A | 6/1993 | Young et al. ............. 424/85.7 |
| 5,286,748 A | 2/1994 | Eby, III ...................... 514/494 |
| 5,482,706 A | 1/1996 | Igari et al. |
| 5,725,852 A | 3/1998 | Igari et al. |
| 5,830,456 A | * 11/1998 | Cummins .................. 424/85.7 |

FOREIGN PATENT DOCUMENTS

| CA | 1320905 | 8/1993 |
| EP | 0 396 903 | 11/1990 |
| EP | 578 823 A1 | 1/1994 |
| JP | 6-298665 | 10/1994 |
| WO | WO 82/00588 | 3/1982 |
| WO | WO 88/03411 | 5/1988 |
| WO | WO 89/06139 | 7/1989 |
| WO | WO 92/10207 | 6/1992 |
| WO | WO 93/21229 | 10/1993 |
| WO | WO 95/27502 | 10/1995 |

OTHER PUBLICATIONS

Wong et al., Ann. Intern. Med., 1995, vol. 122, pp. 664–675.*

Malaguarnera et al., Curr. Ther. Res., 1996, vol. 57, pp. 646–662.*

Babiuch et al., "An Interim Report on the Effect of Natural Human Interferon Alpha (IFN–α) Lozenges in Patients Seropositive for the Human Immunodeficiency Virus Type 1 (HIV–1)", Archivum Immunologiae et Therapiae Experimentalis, 41:213–219 (1993).

Boguniewicz et al., "The Effect of Nebulized Recombinant Interferon–γ in Asthmatic Airways", J. Allergy Clin. Immunol. 95:133–135 (1995).

Brod et al., "Oral Administration of IFN–α is Superior to Subcutaneous Administration of IFN α in the Suppression of Chronic . . . ", Journal of Autoimmunity 9:11–20 (1996).

Douglas et al., "Prophylactic Efficacy of Internasal Alpha$_2$–Interferon Against Rhinovirus Infections in the Family Setting" 314: 65–70 (1986).

Hayden et al., "Intranasal Interferon α2 for Prevention of Rhinovirus Infection and Illness", Journal of Infectious Diseases 148:543–550 (1983).

Hayden et al., "Human Tolerance and Histopathologic Effects of Long Term Administration of Intranasal Interferon–α2", Journal of Infectious Diseases 148:914–921 (1983).

Hayden et al., "Prevention of Natural colds by Contact Prophylaxis with Intranasal Alpha$_2$–Interferon", New England Journal Of Medicine 314:71–75 (1986).

Hayden et al., "Human Nasal Mucosal Responses to Topically Applied Recombinant Leukocyte A Interferon", Journal of Infectious Diseases 156:64–72 (1987).

Iida et al., "Protective Activity of Recombinant Cytokines Against Sendai Virus and Herpes Simplex Virus (HSV) infections in mice", Vaccine 7:229–233 (1989).

Matsuzawa et al., "Protective Effect of Mucosal Administration of Recombinant Human Macrophage Colony–Stimulating Factor . . . ", Vaccine 15:85–89 (1997).

Moore et al., "Inflammatory Markers in Bronchoalveolar Lavage Fluid of Standardbred Racehorses with Inflammatory . . . ", Equine Veterinary Journal 29:142–147 (1997).

Samo et al., "Efficacy and Tolerance of Intranasally Applied Recombinant Leukocyte A Interferon in Normal Volunteers", Journal of Infectious Diseases 148:535–542 (1983).

Samo et al., "Intranasally Applied Recombinant Leukocyte A Interferon in Normal Volunteers. II.", Journal of Infectious Diseases 150:181–188 (1984).

Soos et al., "Oral Feeding of Interferon τ Can Prevent the Acute and Chronic Relapsing Forms of Experimental Allergic Encephalomyelitis", Journal of Neuroimmunology 75:43–50 (1997).

Vriesendorp et al., "Oral Administration of Type I Interferon Modulates the Course of Experimental Allergic Neuritis", Autoimmunity 24:157–165 (1996).

(List continued on next page.)

Primary Examiner—Yvonne Eyler
Assistant Examiner—J. L. Andres
(74) Attorney, Agent, or Firm—Browdy and Neimark PLLC

(57) ABSTRACT

A method for stimulating host defense mechanisms in a mammal via administering to the mammal a therapeutically effective amount of an interferon via oromucosal contact. The amount of interferon administered is less than an amount which induces a pathological response when administered parenterally.

19 Claims, No Drawings

OTHER PUBLICATIONS

Zielinska et al., "Comparison of the Long–Term Effects of Treatment with Oral and Parenteral . . . ", *Archivum Immunologiae et Therapiae Experimentalis* 44:359–366 (1996).

Kaido, T.J., "Intranasal administration of IFN–α/β inhibits the development of visceral tumor metastases," *Journal of Interferon and Cytokine Research*, 17:31–36 (1997).

Yoshino, S., "The preventive effect of oral administration of type 1 interferon on collagen–induced arthritis in rats," *Experimental and Molecular Pathology*, 62:123–130 (1995).

* cited by examiner

STIMULATION OF HOST DEFENSE MECHANISMS AGAINST VIRAL CHALLENGES

This invention relates to methods of stimulation of host defense mechanisms against pathological conditions in a host mammal by administration of interferon via the oromucosa. In particular, the invention is applicable to methods of treatment of autoimmune, mycobacterial, neurodegenerative, parasitic, and viral diseases.

BACKGROUND OF THE INVENTION

Interferon-α (IFN-α) is used widely for the treatment of a variety of disorders including leukemia, lymphoma, AIDS-related Kaposi's sarcoma, and hepatitis. (Gutterman, J. U., *Proc. Natl. Acad Sci. USA*, 1994 91: 1198–1205). Interferon-β (IFN-β) is licensed for clinical use in treatment of relapsing-remitting multiple sclerosis and of chronic infection with Hepatitis B virus. Interferon-α and Interferon-β are both type I interferons. Although a number of routes of administration, including intravenous, subcutaneous, intramuscular, topical, and intralesional injection, are commonly employed for the administration of type I interferons, the oral route has not been generally used, because interferons are proteins which are considered to be inactivated by proteolytic enzymes and which are not absorbed appreciably in their native form in the gastrointestinal tract. Indeed a number of studies have failed to detect interferons in the blood following oral administration (Cantell and Pyhälä, *J Gen. Virol.*, 1973 20: 97–104; Wills et al, *J IFN Res.*, 1984 4: 399–409; Gilson et al, *J IFN Res.*, 1985 5: 403–408).

It has been shown that inducers of interferon are able to protect mice against experimental infection with *Plasmodium berghei* malaria, and that this protection is much more effective against sporozoite-induced infection than against infection induced by blood forms of the parasite (Jahiel et al, *Science*, 1986 16: 1802; *Nature*, 1968 220: 710; *Amer. J. Trop. Med Hyg.*, 1969 18: 823). Mice injected intraperitoneally or intravenously with interferon in pooled serum of Newcastle disease virus-infected mice were protected against sporozoite-induced *Plasmodium berghei* malaria. However, interferon from rabbit serum was ineffective. Protection was obtained when the interferon was injected during the pre-erythrocytic phase of parasite development (i.e. three hours before or up to about 40 hours after sporozoite inoculation [Jahiel et al, *Nature* 1970 227: 1350–1351]).

There have been a number of anecdotal reports of efficacy of low doses of interferon administered as a nasal spray or as an oral liquid formulation in the treatment of a variety of viral conditions, particularly influenza. However, in most of these reports the interferon preparations used were relatively crude. Placebo-controlled trials of high dose intranasal interferon for treatment of rhinovirus infection showed that the treatment was effective, but that there was a significant incidence of side-effects (Hayden et al, *J Infect. Dis.*, 1983 148: 914–921; Douglas et al, *New Engl. J. Med.*, 1986 314: 65–80; Hayden et al; *New Engl. J. Med.*, 1986 314: 71–75).

More recently a series of patent specifications has described the use of low doses of orally administered interferon of heterologous species origin for the treatment of infectious rhinotracheitis ("shipping fever") in cattle, and of feline leukemia, and also treatment of other conditions, for enhancement of efficiency of vaccines; for improving the efficiency of food utilization; and for prevention of bovine theileriosis. See U.S. Pat. No. 4,462,985, Australian Patent No. 608519, Australian Patent No. 583332 and U.S. Pat. No. 5,215,741 respectively. In these specifications, the interferon used was human interferon α prepared by the method of Cantell, administered in phosphate buffered saline, at a dose of 0.01 to 5 IU per pound body weight. While these specifications suggest that such low doses of interferon administered to the oropharyngeal mucosa, preferably in a form adapted for prolonged contact with the oral mucosa, may be efficacious for treatment of a wide variety of conditions, the experimental evidence for conditions other than shipping fever, feline leukemia, canine parvovirus and theileriosis is largely anecdotal.

More recent studies on the effects of very low doses of interferon administered by the oral or oropharyngeal mucosa have been reviewed (Bocci, *Clin. Pharmacokinet.*, 1991 21: 411–417; *Critic. Rev. Therap. Drug Carrier Systems*, 1992 9: 91–133; Cummins and Georgiades, *Archivum Immun. Therap. Exp.*, 1993 41: 169–172). It has been proposed that this type of treatment is particularly useful for treatment of HIV infection, and can at least improve quality of life in AIDS patients (Kaiser et al, *AIDS*, 1992 6: 563–569; Koech et al, *Mol. Biol. Ther.*, 1990 2: 91–95). However, other reports indicate that such treatments provide no clinical benefit. A Phase I study of use of oral lozenges containing low doses of interferon for treatment of hepatitis B has also been reported (Zielinska et al, *Archiv. Immunol Therap. Exp.*, 1993 41: 241–252).

SUMMARY OF THE INVENTION

This invention provides a method for stimulating host defense mechanisms in a mammal via the oromucosal administration of an interferon. In one aspect, the invention may be considered as a method of stimulating the immune response in a mammal by administering to the mammal an immunostimulating amount of an interferon via oromucosal contact.

This invention provides a method for treating autoimmune, mycobacterial, neurodegenerative, parasitic, and viral diseases in a mammal via administering to the mammal a therapeutically effective amount of an interferon via oromucosal contact. The amount of interferon administered is less than an amount which induces a pathological response when administered parenterally. This invention provides a method for treating autoimmune diseases such as arthritis, diabetes, lupus, and multiple sclerosis, mycobacterial diseases such as leprosy and tuberculosis, neurodegenerative disorders such as encephalitis and Creutzfeldt-Jakob syndrome, parasitic diseases such as malaria, and viral diseases such as cervical cancer, genital herpes, hepatitis B and C, HIV, HPV, and HSV-1 and 2.

The oromucosal administration may involve administering an effective dose of interferon in a single dose or the effective dose may be administered in a plurality of smaller doses over a period of time sufficient to elicit host defense stimulation equivalent to that of a single dose. Likewise, the effective dose of interferon may be administered continuously over a period of time sufficient to elicit host defense stimulation equivalent to that of a single dose.

The method may be practiced by administering from about 1500 IU, preferably from about 5000 IU, to about $20 \times 10^6$ IU of interferon per day, more preferably from about $1 \times 10^4$ IU to about $20 \times 10^6$ IU of interferon per day, most preferably from about $1 \times 10^4$ to about $1 \times 10^6$ IU of interferon per day, provided that the chosen dose does not induce a pathological response when administered parenterally, or is less than a dose which would induce a pathological response when administered parenterally. These dose ranges generally refer to homologous interferon a in man. A physician treating a patient with a particular interferon will be able to readily identify the suitable therapeutic dose range according to the invention.

In another embodiment, the invention provides a pharmaceutical composition for oromucosal administration comprising a therapeutically effective amount of at least one interferon. The composition may be provided as a solution, tablet, lozenge, gel, syrup, paste, or controlled release oromucosal delivery system. Optionally, the composition may contain buffers, stabilizers, thickening agents, absorption, and viscosity enhancers, and the like.

In one embodiment, the pharmaceutical composition is provided in unit dosage form having from about 1500 IU, preferably from about 5000 IU, to about $20 \times 10^6$ IU of interferon, more preferably from about $1 \times 10^4$ IU to about $20 \times 10^6$ IU of interferon, most preferably from about $1 \times 10^4$ to about $1 \times 10^6$ IU of interferon.

The method may be practiced either as the sole therapeutic approach, or as an adjunct to other therapy, or with other cytokines, such as interleukin-2, 12, or 15, or with IFN-inducers.

The method is conducted using a Type I or II interferon, selected from α, β, γ, ω, and consensus interferons, most preferably with a recombinant IFN-α.

DETAILED DESCRIPTION OF THE INVENTION

The invention will now be described in detail by way of reference only using the following definitions and examples. All patents and publications referred to herein are expressly incorporated by reference.

Definitions

As used herein, "interferon" refers to a Type I or Type II interferon, including those commonly designated as α, β, γ, and ω, and mixtures thereof, including the consensus sequence. Interferons are available from a wide variety of commercial sources and are approved for the treatment of numerous indications. The interferon may be from natural sources, but is preferably a recombinant product. For the purposes of the invention, the term "interferon" also includes polypeptides or their fragments which have interferon activity, and chimeric or mutant forms of interferon in which sequence modifications have been introduced, for example to enhance stability, without affecting the nature of their biological activity, such as disclosed in U.S. Pat. Nos. 5,582,824, 5,593,667, and U.S. Pat. No. 5,594,107 among others.

While it is to be clearly understood that the invention is applicable to any pathological condition in which stimulation of host defense mechanisms or immunostimualtion is beneficial, preferably the pathological condition is an autoimmune disease or a viral or parasitic infection. It will also be understood that for the purposes of the invention the interferon may be used either alone or in conjunction with another agent or treatment.

Optionally the interferon may be administered concurrently with an inducer of interferon synthesis and release. The inducer may be administered together with the interferon, or may be administered separately. A variety of inducers of interferon is known, for example polynucleotides such as poly I:C; preferably a low molecular weight, orally administrable interferon inducer is used. Suitable inducers are known in the art, for example Tilorone (U.S. Pat. No 3,592,819; Albrecht et al, *J. Med. Chem.* 1974 17: 1150–1156) and the quinolone derivative Imiquimod (Savage et al; *Brit. J. Cancer*, 1996 74: 1482–1486).

The methods and compositions of the invention may optionally be used in conjunction with one or more other treatments for the specific condition, and the attending physician or veterinarian will readily be able to select such other treatment as may be appropriate in the circumstances.

The viral condition may be an acute or fulninant infection, such as rhinovirus, influenza, herpes varicella, herpes zoster, dengue fever, or viral encephalitis including but not limited to measles virus encephalitis, Murray Valley encephalitis, Japanese B encephalitis, tick-borne encephalitis and Herpes encephalitis; haemorrhagic fevers such as Ebola virus, Marburg virus, Lassa fever; Hanta virus infections, and other viral infections thought to be transmitted from animals to humans, such as equine morbillivirus. In many of these conditions there is no treatment and/or vaccine presently available, and supportive treatments may be inadequate. Alternatively the viral condition may be the result of chronic infection, such as hepatitis B, hepatitis C, hepatitis D or other forms of viral hepatitis, and CMV, HIV, HPV, and HSV I & II infection. Hepatitis B and hepatitis C are both currently treated with parenteral interferon; long-term interferon treatment in HIV infection which has progressed to AIDS is under clinical trial.

In a second embodiment, the disease to be treated is malaria, and again a Type I or II interferon is administered as described above. The causative organism of the malaria may be *Plasmodium malariae, Plasmodium vivax, Plasmodiumfalciparum* or *Plasmodium ovale*. It is particularly contemplated that the method of the invention will protect against progression of malaria to the cerebral form.

In a third embodiment, the invention provides a method of treatment of autoimmune disorders such as HIV, rheumatoid arthritis, and multiple sclerosis, whether of the relapsing-remitting or the chronic progressive type, or immunodeficiencies such as AIDS, comprising the step of administering an interferon as described above.

Again the method and dosage form of the invention may be used in conjunction with other treatments. For example, for herpes virus infection acyclovir or ganciclovir may be used. For HIV infection azidothymidine (zidovudine) or one or more other HIV reverse transcriptase inhibitors, and/or HIV protease inhibitors may be used.

In the preparation of the pharmaceutical compositions of this invention, a variety of vehicles and excipients for IFN may be used, as will be apparent to the skilled artisan. Representative formulation technology is taught in, inter alia, Remington: The Science and Practice of Pharmacy, 19th ed., Mack Publishing Co., Easton, Pa, 1995, and its predecessor editions. The IFN formulation may comprise stability enhancers, such as glycine or alanine, as described in U.S. Pat. No. 4,496,537, and/or one or more carriers, such as a carrier protein. For example, for treatment of humans pharmaceutical grade human serum albumin, optionally together with phosphate-buffered saline as diluent, is commonly used. Where the excipient for IFN is human serum albumin, the human serum albumin may be derived from human serum, or may be of recombinant origin. Normally when serum albumin is used it will be of homologous origin.

The IFN may be administered by any means which provides contact of the IFN with the oromucosal cavity of the recipient. Thus it will be clearly understood that the invention is not limited to any particular type of formulation. The present specification describes administration of IFN deep into the oromucosal cavity; this may be achieved with liquids, solids, or aerosols, as well as nasal drops or sprays. Thus the invention includes, but is not limited to, liquid, spray, syrup, lozenges, buccal tablets, and nebuliser formulations. A person skilled in the art will recognize that for aerosol or nebuliser formulations the particle size of the preparation may be important, and will be aware of suitable methods by which particle size may be modified.

In one aspect, the interferon is administered in a single dose. Alternatively, the interferon is administered in a plurality of lower doses, distributed over time, so that the net effect is equivalent to the administration of the single higher dose. One approach to this delivery mode is via the provision of a sustained or controlled release device adhered to or implanted in the oromucosal cavity and designed to release interferon over time in an amount equivalent to a single high dose.

Representative formulations of interferon for oromucosal use include the following (all % are w/w):

Tablet: Dextrose BP 45%; gelatin BP 30%; wheat starch BP 11%; carmellose sodium BP 5%; egg albumin BPC 4%; leucine USP 3%; propylene glycol BP 2%; and $10^6$ IU IFN-α2. The tablet may be used as is and allowed to slowly dissolve in the mouth or may be dissolved in water and held in the mouth as needed.

An interferon paste may be prepared, as described in U.S. Pat. No. 4,675,184, from glycerin 45%, sodium CMC 2%, citrate buffer (pH 4.5) 25%, distilled water to 100%, and $10^6$ IU IFN-α2. The interferon paste may be adhered to the buccal mucosa.

Likewise, a gargle or a syrup may be prepared by adding the desired amount of interferon to a commercially available mouthwash or cough syrup formulation.

Within the specific dose ranges referred to above, the optimal treatment in any individual case will depend on the nature of the condition concerned, the stage of disease, previous therapy, other continuing therapy, the general state of health of the mammal, the sensitivity of the subject to interferon, etc., and therefore will be at the physician's or veterinarian's discretion, bearing in mind all these circumstances. The length of treatment will of course vary with the condition being treated, for example, treatment of an acute infection, such as Ebola virus, would be expected to involve a different course of treatment than treatment of a chronic condition, such as hepatitis.

The effective dose disclosed herein is one which does not generate a pathological response in the mammal when administered parenterally. A pathological response may be acute, chronic, or cumulative, and may be manifested by changes in blood chemistry, such as leukopenia, bone marrow depression, or other histological parameters. As used herein, a pathological response includes adverse side effects, such as fever, malaise, or flu-like symptoms, vascular reactions, such as phlebitis, and local inflammatory reactions at the site of injection. Such responses will vary considerably among the patient population in view of individual variations in sensitivity to interferon. A simple test for identifying an acceptable low dose of interferon for oromucosal therapy is to inject the patient with the putative acceptable dose, based upon considerations of age, weight, indication, progression, etc. and ascertain if the injection produces a pathological response as defined herein, with local irritation at the site of injection being the most readily ascertainable criterion. If no adverse response is noted, then the same dose may be administered oromucosally. If there is an undesirable response, then the process is repeated at a lower dose, until a non-pathological dose is identified.

For many patients, it is expected that oromucosal doses will be approximately the same as those known to be well tolerated and effective in existing approved parenteral protocols. Therefore, for purposes of specificity, an acceptable low dose of interferon may be from about 1500 IU, preferably from about 5000 IU, to about $20 \times 10^6$ IU of interferon. More preferably the dose is from about $1 \times 10^4$ IU to about $20 \times 10^6$ IU of interferon, most preferably from about $1 \times 10^4$ IU to about $1 \times 10^6$ IU of interferon, provided that the dose is one which does not induce a pathological response when administered parenterally. In one embodiment, the total dose may be administered in multiple lower doses over time, or even may be delivered continuously or in a pulsatile manner from a controlled release device adhered to or implanted in the oromucosa.

INTERFERONS AND INTERFERON FORMULATIONS

Mouse IFN-α/β

Mouse IFN-α/β (Mu IFN-α/β) was prepared from cultures of C243-3 cells induced with Newcastle disease virus (NDV) and purified as described previously (Tovey et al, *Proc. Soc. Exap. Biol. and Med.*, 1974 146: 809–815). The preparation used in this study had a titer of $4 \times 10^6$ International Units (IU)/ml and a specific activity of $5 \times 10^7$ IU/mg protein as assayed on mouse 929 cells challenged with vesicular stomatitis virus (VSV) as described previously (Tovey et al, *Proc. Soc. Exp. Biol. and Med.*, 1974 146: 809–815). The preparation was standardized against the international reference preparation of murine IFN-α/β of the National Institutes of Health (NIH) (G-002-9004-5411).

Human IFN-α 1–8

Recombinant human IFN-α 1–8 (Hu IFNα 1–8; BDBB lot no. CGP 35269-1, Ciba-Geigy, Basel, Switzerland) was prepared and purified as described previously (Meister et al, *J Gen. Virol.*, 1986 67: 1633–1643). The preparation used in this study had a titer of $70 \times 10^6$ IU/ml on homologous human WISH cells challenged with VSV as described previously (Tovey et al, *Nature*, 1977 267: 455–457), and a titer on heterologous mouse L929 cells of $1 \times 10$ IU/ml. The preparation was standardized against both the NIH human IFN-α international reference preparation (G-023-901-527) and the NIH murine IFN-α/β standard (G-002-9004-5411). The specific activity of the IFN preparation was $2 \times 10^8$ IU/mg protein.

RECOMBINANT MURINE INTERFERON-α

Recombinant murine interferon-α was purchased from Life Technologies Inc. The preparation used in this study (lot no. HKK404) had a titer of $6 \times 10^6$ IU/ml and a specific activity of $6 \times 10^8$ IU/mg protein as assayed on mouse L929 cells challenged with VSV (Tovey et al, *Proc. Soc. Exp. Biol. Med.*, 1974, 146:406–415).

RECOMBINANT MURINE INTERFERON β

Recombinant murine interferon β was purchased from R & D Systems Inc. The preparation used in this study (lot no. 1976-01S) had a titer of $3.2 \times 10^4$ IU/ml and a specific activity of $8 \times 10^6$ IU/mg protein as assayed on mouse L929 cells challenged with VSV (Tovey et al, *Proc. Soc. Exp. Biol. Med.*, 1974, 146:406–415).

RECOMBINANT MURINE INTERFERON γ

Recombinant murine interferon γ was purchased from R & D Systems Inc. The preparation used in this study (2580-03SA) had a titer of $2 \times 10^5$ IV/ml and a specific activity of $1 \times 10^7$ IU/mg protein as assayed on mouse L929 cells challenged with VSV (Tovey et al, *Proc. Soc. Exp. Biol. Med.*, 1974, 146:406–415).

All the interferon preparations were titrated simultaneously in the same assay and standardized against the international reference preparation of murine interferon α/β of the US National Institutes of Health (G-002-9004-5411).

EXCIPIENT

Interferon preparations were diluted in phosphate buffered saline (PBS) containing bovine serum albumin (BSA) or a proprietary excipient. Bovine serum albumin fraction V (RIA grade; immunoglobulin free; Cat. no. A7888; Sigma; USA) was dissolved at a final concentration of 100 μg/ml in PBS (pH 7.4) and sterilized by filtration (0.2 μl, Millex-GV, Millipore, USA). The proprietary excipient used was as follows, supplied in the form of tablets (Ferimmune™, Pharma Pacific):

|  | % w/w | mg/tablet |
| --- | --- | --- |
| Dextrose (Glucose) BP** | 44.67*** | 55.84 |
| Gelatin BP** | 30.06 | 37.58 |
| Wheat Starch BP** | 11.31 | 14.14 |
| Carmellose Sodium BP** | 4.96 | 6.20 |
| Egg Albumen BPC** | 4.03 | 5.04 |
| Leucine USP | 3.00 | 3.75 |
| Propylene Glycol BP | 1.88 | 2.35 |
| Dextran 40** | 0.06 | 0.08 |
| (as Dextran 40 Injection BP) |  |  |
| Sodium Phosphate BP | 0.03 | 0.04 |
| Sodium Chloride BP | 0.01 | 0.01 |
| Sodium Acid Phosphate BP | 0.01 | 0.01 |
| Total | 100.02 | 125.04 |

**Calculated on an anhydrous basis
***Derived from:
Dextrose (Glucose) BP (anhydrous) 44.64%
Glucose BP (as Dextran 40 Injection BP) 0.03%

A single tablet was dissolved in 1.5 ml phosphate buffered saline, centrifuged at 16,000 g for 15 m, and then sterile filtered (0.2 μ, Millex-GV, Millipore, USA), and stored at 4° C. prior to use. Excipient was prepared daily prior to use.

INTERFERON DELIVERY SYSTEM

Preliminary experiments showed that the application of 5 μl of crystal violet to each nostril of a normal adult mouse using a P20 Eppendorf micropipette resulted in an almost immediate distribution of the dye over the whole surface of the oropharyngeal cavity. Staining of the oropharyngeal cavity was still apparent some 30 minutes after application of the dye. Essentially similar results were obtained using $^{125}$I-labelled recombinant human IFN-α 1–8 applied in the same manner. This method of administration was therefore used in all subsequent experiments.

For the purposes of the animal experiments described in this specification, it will be clearly understood that the expression "intranasal/oral" or "intranasal plus oral" or "in/or" or "oromucosal" or "oropharyngeal" with reference to the route of administration of IFN is to be taken to mean administration of the IFN preparation deep into the nasal cavity so that it is rapidly distributed into the oropharyngeal cavity, i.e. the mouth and throat of the recipient mammal, so as to make contact with the mucosa lining this cavity.

EMCV (ENCEPHALOMYOCARDITIS VIRUS)

Batch: Lot no. 095001
Expiration Date: December 1997

Preparation: EMCV strain JH was propagated on mouse L929 cells using methods described previously (Gresser I. Bourali C, Thomas M T, Falcoff E. Effect of repeated inoculation of interferon preparations on infection of mice with Encephalomyocarditis virus. *Proc Soc Exp Biol Med* 1968 February; 127:491–6)

Characterization: The virus stock used in this study had a titer of $5 \times 10^{8.62}$ TCID$_{50}$ on mouse L929 cells.

Storage: Stock EMCV was stored at −70° C. A power cut on day 1 of the Virus Titration necessitated transfer temporarily to back-up storage at approximately the same temperatures. The material remained frozen at all times. On day +8 of the Virus Titration the −70° C. freezer increased in temperature to −60° C. Diluted EMCV was prepared immediately before use and was kept on ice or in the animal room refrigerator until use.

ANIMALS

The mice used in this study were obtained from a specific pathogen-free colony (IFFA CREDO, France). They were housed in a specific pathogen-free animal facility at the Institut Federatif CNRS at Villejuif according to EEC standards.

INTERFERON BIOASSAY

Interferon was assayed according to a conventional method. Briefly, samples (20 μl) were diluted in 80 μl of Eagle's Minimal Essential Medium (MEM) (Gibco, France) containing 2% heat-inactivated Fetal Calf Serum (FCS) (Gibco, France) and added to each well of a microtiter plate (Falcon, cat. no. 3072) using a multichannel micro-pipette (Finnpipette, Labsystem, 50–300 μl). WISH or L929 cells ($2 \times 10^4$ cells/well) were added in 100 μl of MEM containing 2% FCS and incubated overnight at 37° C. in an atmosphere of 5% $CO_2$ in air (Forma 3029 $CO_2$ incubator). The cells were then examined for any signs of toxicity using an Olympus IM GLDW inverted microscope equipped with a 10x objective. Samples which did not exhibit detectable toxicity were then subjected to serial two-fold dilutions starting from an initial 1:10 dilution in a total volume of 200 μl of Eagle's MEM containing 2% FCS, by carrying forward 100 μl of diluted material with a multichannel micropipette, in a microplate containing 100 μl per well of fresh Eagle's MEM containing 2% FCS. Appropriate serial two-fold dilutions of the NIH human IFN-α reference standard (G-023-901-527) or the NIH Mu IFN-α/β reference standard (G002-9004-5411) were also prepared. WISH or L929 cells ($2 \times 10^4$ cells/well) in 100 μl of Eagle's MEM containing 2% FCS were then added to each plate where appropriate and incubated overnight at 37° C. in an atmosphere of 5% $CO_2$ in air. The cell monolayers were then checked for any signs of toxicity and in the absence of any apparent toxicity, the culture was aspirated and replaced with 200 μl of Eagle's MEM containing 2% FCS containing 100 TCID$_{50}$ of VSV ($2 \times 10^{-4}$ VSV$_{23}$ for WISH cells, or $10^{-5}$ VSV$_{23}$ for L929 cells). The plates were then incubated overnight at 37° C. in an atmosphere of 5% $CO_2$ in air. The cell monolayers were then examined for specific viral cytopathic effect using an Olympus IM ULWD inverted microscope. Interferon titers were determined from the reciprocal of the dilution which gave 50% protection against specific viral cytopathic effect, and are expressed in international reference units/ml (IU/ml).

EXAMPLE 1

Effect of Oromucosal Interferon Against Viral Infection

Intraperitoneal infection of mice with Encephalomyocarditis virus (EMCV) gives rise to a rapidly progressing fatal disease characterized by CNS involvement and encephalitis (Rueckart, R. R., in Virology, Fields ed., 705–738, 1985, Raven Press, New York). IFN-α has been shown to be effective in protecting mice against lethal EMCV infection when administered either prophylactically or even when administered after virus replication has already occurred in target organs (Finter, N. B.; Front. of Biol., 1973 2 135–147). Thus, in these studies we determined the effect of oromucosally administered low doses of either natural or recombinant IFNs on the survival of mice injected with a lethal dose of EMCV, ie. in a very severe test of antiviral activity.

Encephalomyocarditis virus strain (JH) was propagated on mouse L929 cells as described previously (Gresser et al; *Proc. Soc. Exp. Biol and Med.*, 1968 127: 491–496). The virus stock used in this study (EMC-α) had a titer of $5 \times 10^{8.62}$ TCID$_{50}$ on mouse L929 cells.

Treatment of mice with 200 or 2000 IU of Mu IFN-α/β or Hu IFN-α 1–8 via the in/or route increased the mean survival time of mice infected with a lethal dose of EMCV (300 LD$_{50}$). In all experiments Hu IFN-α/β 1–8 was as effective as Mu IFN-α/β.

The administration of the IFNs by the in/or route resulted in a statistically significant increase in the mean survival time in 6 of the 9 experiments carried out in this study, for example from 5.0±0.4 days (control) to 9.2±2.3 days (2000 IU). Furthermore, the overall trend was towards efficacy in all the experiments undertaken. Administration by the ip route (200 μl per injection) resulted in a significant increase in the mean survival time in 7 of the 8 experiments undertaken in this study using ip administration.

Where ip and in/or administration can be directly compared, the ip route is marginally more effective (7/16 cases) or not significantly different (9/16 cases).

EXAMPLE 2

Effect of Oromucosal Interferon Against Vesicular Stomatitis Virus

Groups of ten, 6 week-old mice, from a specific pathogen-free breeding colony were infected intranasally with 100 LD50 of Vesicular Stomatitis virus (VSV) (Tovey et al, *Proc. Soc. Exp. Biol Med.*, 1974, 146:406–415), in a volume of 10 μl. Seven hours after virus infection mice were either left untreated, or treated once a day for 4 days by the intranasal/oral route with a given dose of murine interferon I/9 in a volume of 10 μl of Ferimmune™ excipient, or with 10 μl of excipient alone (control).

Treatment of adult mice with murine interferon α/β resulted in a marked increase in the percentage of animals surviving infection with a lethal dose of VSV. Thus, 30% of the animals treated with 10,000 IU of interferon α/β were alive 21 days after infection with a lethal dose of VSV, under conditions where all the untreated, or excipient control treated virus-infected animals were dead at 10 days. Clinical observations suggest that most of the interferon-treated animals alive at 21 days will survive.

EXAMPLE 3

Effect of Oromucosal Interferon on Expression of Cellular Proteins

IFN-α is known to induce the expression of a number of cellular proteins following binding of the protein to its cell surface receptor. These proteins are thought to provide a useful marker of IFN action.

We evaluated the effect of IFN-α administered via the in/or route on the expression of three IFN-induced proteins, MHC class I antigens, Ly 6A/E antigen and 2'-5'-oligoadenylate synthetase.

Treatment of DBA-2 mice (H-2K$^d$) with up to 20,000 IU of Mu IFN-α by the in/or route did not significantly increase H-2-K$^d$ expression on peripheral blood lymphocytes, monocytes or granulocytes under conditions where as little as 20 1IU of Mu IFN-α given ip markedly increased the expression of H-2-K$^d$ antigens on both peripheral blood monocytes and granulocytes. Indeed, expression on monocytes was slightly suppressed.

Similarly, treatment of mice with up to 20,000 IU of IFN-α via the in/or route had no significant effect on the expression of Ly6 A/E antigens, the expression of which is markedly enhanced on the surface of a variety of lymphoid cells following parenteral treatment with type I IFN (Dumont et al; *J Immunol*, 1986 137: 201–210). Similar results were obtained with 200 or 20,000 IU of either Mu IFN-α or Hu IFN-α 1–8 via the in/or route.

Treatment of either Swiss or DBA/2 mice with as little as 20 IU of Mu IFN-α injected ip resulted in a marked increase in 2'-5'-oligoadenylate synthetase activity in both peripheral blood mononuclear cells and splenocytes. In contrast, in the same experiment treatment of mice with up to 20,000 IU of Mu IFN-α via the in/or route did not significantly increase the expression of 2'-5'-oligoadenylate synthetase activity. Furthermore, treatment with 200 or 20,000 IU of either Mu IFN-α or Hu IFN-α 1–8 by the in/or route had no significant effect on 2'-5'-oligoadenylate synthetase activity at any of the time points tested up to 10 days after the start of IFN treatment.

EXAMPLE 4

Bioavailability of Interferon Following Oromucosal Administration

In order to examine the bioavailability and pharmacokinetics of IFN, mice, which have the most favorable drug-blood volume ratio for such studies, were treated with a single high dose of recombinant IFN-α labelled to the highest specific radioactivity possible with $^{125}$I.

A pure preparation of $70 \times 10^6$ IU of Hu IFN-α 1–8 was taken up in 1.4 mls of PBS, and iodinated as described by Mogensen et al, (*Int. J Cancer*, 1981 28: 575–582) using a modification of the chloramine-T method described by Hunter and Greenwood (*Nature*, 1962 194: 495–496).

The $^{125}$I-labelled Hu IFN-α 1–8. (lot no. CGP35269-1) exhibited a biological activity of $2 \times 10^7$ IU/ml when assayed on human WISH cells challenged with VSV and $1 \times 10^6$ IU/ml when assayed on mouse L929 cells challenged with VSV.

Six to seven week-old female Swiss mice were injected iv, ip, or treated in/or with $2 \times 10^7$ IU equivalent to 1 $\times 10^6$ murine IU of $^{125}$Hu IFN-α 1–8($1.0369 \times 10^7$ cpm/mouse). At the time points indicated, three mice per group were sacrificed, blood was collected, and the volume determined. Kidney, liver, lung, spleen, and stomach/oesophagus were harvested, blotted, and weighed to a precision of ±1.0 μg. The radioactivity of each sample was determined individually using a gamma counter. Whole blood was then separated by centrifugation (800 g×10 min., 4° C.), the serum was harvested, counted, and frozen at −80° C. The serum was then assayed for IFN content using a standard bioassay on both human WISH cells and on mouse L929 cells as described above. The radioactive material present in the samples of serum was then isolated by affinity immunoprecipitation and analyzed by SDS-PAGE.

Very high levels of radioactivity (>2×10$^6$ cpm/ml) were detected in the peripheral blood of animals 5 min. after injection of 1.0369×10$^7$ cpm/mouse of $^{125}$I-labelled Hu IFN-α 1–8 by iv bolus. The amount of radioactivity present in whole blood then declined progressively at 15 and 30 min. The levels of radioactivity detected in the peripheral blood of animals 5 min. after ip injection of 1.0369×10$^7$ cpm of $^{125}$I Hu IFN-α 1–8 were approximately twenty fold lower than the levels detected following an iv bolus. The levels of radioactivity then increased progressively at 15 and 30 min. post-injection. The levels of radioactivity detected in the blood of animals at 5, 10 or 15 min. after the in/or administration of $^{125}$I IFN-α 1–8 were significantly lower than those detected at a given time following ip injection of the same quantity of radiolabelled IFN. For all three routes of administration, higher levels of radioactivity were detected in serum than in whole blood following in/or administration of $^{125}$I-labelled IFN-α 1–8. The lower levels of radioactivity detected per ml of whole blood compared with the same volume of serum reflect the effectively larger volume of serum counted after removal of the cellular component of whole blood.

Samples of serum from all the mice in the study were assayed for the presence of biologically active IFN using a standard bioassay, as described above, and showed readily detectable levels of biologically active IFN in the serum of all the animals injected either iv or ip with $^{125}$I Hu IFN-α 1–8 at all the time points tested. In contrast, no biologically active IFN was detected in the serum of any of the animals at any of the time points tested following the in/or administration of IFN, in spite of the presence of relatively high levels of radioactivity in the serum of these animals.

In order to determine whether the radioactive material detected in the serum of animals treated with $^{125}$I Hu IFN-α 1–8 does indeed represent native IFN, the samples were immunoprecipitated with protein A-G Agarose, in order to precipitate immunoglobulins present in the samples, treated with an affinity-purified polyclonal anti-IFN-α antibody, and further immunoprecipitated. The samples were then subjected to SDS-polyacrylamide gel electrophoresis (SDS-PAGE) as described above.

SDS-PAGE analysis of the radioactive material in serum following iv or ip injection of $^{125}$I Hu IFN-α 1–8 revealed a single homogenous band migrating with an electrophoretic mobility identical to that of uninjected $^{125}$I Hu IFN-α 1–8. The apparent molecular weight of the material was estimated to be approximately 20000 Daltons, which corresponds exactly to the molecular weight of native Hu IFN-α 1–8. In contrast, none of the samples of serum from mice treated in/or with $^{125}$I IFN-α 1–8 contained any material with an apparent molecular weight similar to that of native IFN, even though an identical quantity of radioactive material was loaded on to each gel.

The tissue distribution of radiolabelled material revealed very high levels of radioactivity in the kidneys, high levels in the liver, lung, and spleen of animals 5 min. after the iv injection of $^{125}$I IFN-α 1–8. The level of radioactivity present in each of these four organs was then found to decrease progressively at 15 and 30 min. In contrast, the level of radioactivity in the stomach increased progressively at 15 and 30 min. to reach a level comparable to that present in the serum of animals 30 min. after an iv bolus.

Administration of $^{125}$I IFN-α 1–8 by ip injection resulted in peak levels of radioactivity in all the tissues examined within 15 min., followed by a decline at 30 min. Similarly, in/or administration of $^{125}$I Hu IFN-α 1–8 resulted in peak levels of radioactivity in all the tissues studied after 15 min. with some decline in the levels of radioactivity present at 30 min. The levels of radioactivity present in the stomach/oesophagus were an order of magnitude greater than those detected in any other organ following the in/or administration of $^{125}$I-labelled IFN-α 1–8, and were markedly higher than the levels present in these tissues following parenteral administration of the same quantity of radiolabelled Hu IFN-α 1–8 by either the iv or ip routes.

EXAMPLE 5

Pharmacokinetics of Interferon Following Intranasal/Oral Administration

For precise determination of the pharmacokinetics of Hu IFN-α 1–8, mice were treated iv, ip or in/or with 1.0369×10$^7$ cpm/mouse of $^{125}$I-labelled Hu IFN-α 1–8, and the levels of radioactivity present in both whole blood and serum were determined at a series of time points over a 24 hour period.

The pharmacokinetic profile of $^{125}$I-labelled Hu IFN-α 1–8 present in the blood of mice after an iv bolus closely followed a logarithmic clearance curve. This agreed with results of a previous study carried out in mice using a closely related molecule, recombinant human α A/D (Bgl) (Bohoslawed et al; *J IFN Res.*, 1986 6: 207–213). The amount of bioavailable material, calculated from the area under the cure of concentration versus time, was also similar to that for human α A/D. A biphasic time-consuming clearance curve was observed following an iv bolus of $^{125}$I IFN-α 1–8, which is characteristic of substances which are cleared through the kidneys, in agreement with the results of Example 4. The phannacokinetics of 125I-labelled IFN-α 1–8 following ip injection closely resembled those previously reported for IFNs administered im.

Readily detectable levels of biologically active IFN were present in the serum of all the animals following either an iv bolus or ip injection of $^{125}$I-labelled IFN-α 1–8. Although antiviral activity could not be detected in the serum of animals following in/or administration of $^{125}$I IFN-α 1–8, a statistically significant degree of protection against infection with a lethal dose of EMCV was nevertheless observed in these animals.

Discussion

Our results obtained in a well-defined preclinical model of acute viral infection provided unequivocal evidence to support the "proof of principle" for the use of low dose oromucosal IFN for the therapy of acute systemic viral infections in man, and show that both a natural mixture of multiple IFN-α subtypes and a single recombinant IFN-α isotype (for example Mu IFN-α) exert statistically significant antiviral activity in this model. Natural Mu IFN-α/β and Hu IFN-α 1–8 appeared to be equally effective when administered oromucosally. Recombinant Mu IFN-β and Mu IFN-γ also show similar antiviral activity.

Comparison of the degree of protection obtained when a given type and dose of IFN was administered by the oromucosal route compared to the results obtained following systemic administration (ip injection) showed that parenteral administration of IFN was in some cases marginally more effective, and in other cases no more effective, than oromucosal administration.

The results of the biomarker pilot study (Example 3) show quite clearly that none of the three biomarkers tested (MHC class I antigen, Ly6 A/E antigen, and 2'–5'-oligoadenylate synthetase activity) adequately reflects the very marked antiviral activity exhibited by IFN-α administered by the in/or route.

The contrast between the very marked increase in the expression of all three IFN-induced proteins observed in all the experiments undertaken following the ip injection of as little as 20 IU of IFN-α and the absence of any detectable effect following the administration of up to 20,000 IU of IFN-α via the oromucosal route is striking.

Although we cannot exclude the possibility that an effect on one or other of the biomarkers would have been observed at an earlier or intermediate time point, this seems to be unlikely, as IFN acts on the transcription of the genes coding for these proteins and thus one would not expect to see an effect on any of these biomarkers until a number of hours after IFN treatment.

Again, although we cannot exclude the possibility that a systemic effect on one of the other numerous IFN-induced proteins would have been observed following treatment with IFN-α by the in/or route, this seems unlikely, as this would imply a differential regulation of the expression of certain IFN-induced genes. It is entirely possible, however, that an effect on an IFN biomarker may be observed locally, for example, in nasal lymphocytes following administration of IFN-α via the in/or route.

In keeping with the absence of a detectable effect on the biomarkers studied, no consistent effect was observed on any of the hematological or blood chemistry parameters monitored during oromucosal IFN therapy, even in animals treated with up to 20,000 IU of IFN-α.

The results of the pharmacokinetics-bioactivity study show quite clearly that a statistically significant antiviral effect can be obtained following the oromucosal administration of a single dose of radiolabelled Hu IFN-α 1–8 under conditions where no circulating IFN can be detected in the peripheral blood, using methods of detection which are an order of magnitude more sensitive than those used previously. In keeping with these results the extent of the antiviral activity exerted by oromucosally administered IFN did appear to follow a classical dose-response relationship.

Readily detectable levels of radiolabelled material were found in both whole blood and serum of animals following in/or administration of 125I-labelled IFN-α 1–8. These results contrast with the results of previous studies, which failed to detect IFN in the serum of animals even after the oral administration of large quantities of unlabelled IFN. However, the radioactive material detected in both whole blood and serum following in/or administration was biologically inactive. Furthermore, the results of SDS-PAGE analysis showed that this material was of low molecular weight, and most probably reflected the absorption of degradation products following digestion of IFN in the stomach and small intestine. Analysis of the tissue distribution of radiolabelled material following in/or administration revealed markedly higher levels of radioactivity in the stomach than in any of the other organs tested.

Our results show quite clearly that even though biologically active IFN was not absorbed following in/or administration, this treatment does nevertheless exert a statistically significant antiviral activity in vivo.

Without wishing to be bound by any proposed mechanism for the observed beneficial effect, our results suggest that oromucosally administered IFN exerts its effects against viruses via a presently undefined novel mechanism, which does not involve a direct action of exogenously administered IFN, or the induction of endogenous IFN. This is supported by the absence of detectable levels of circulatory IFN or of the three biomarkers tested. It appears that this mechanism may act at least partly by stimulation of the abundant lymphoid tissue surrounding the nasopharyngeal and oral cavities. Since we have shown that oromucosal IFN is at least comparable in efficacy to systemically administered IFN, our results provide strong support for administration of IFN by the oromucosal route in the treatment of acute viral infections. This could have important implications for the clinical use of IFN.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A method for stimulating systemic host defense mechanisms against a pathogenic condition in a mammal, which method comprises administering to the mammal having such a condition a therapeutically effective amount of an interferon via oromucosal contact, said amount being from about 21.4 IU/kg/day to about $2.9 \times 10^4$ IU/kg/day, where said amount is less than an amount which induces a pathological response in the mammal when administered parenterally, said oromucosal administration being such that it does not involve direct action of the interferon on virally infected cells, and provided that when the condition is rhinovirus, the interferon is not administered through the mouth by multiple or continuous doses.

2. A method of claim 1 in which the effective amount of interferon is administered in a single dose.

3. A method of claim 1 in which the effective amount of interferon is administered in a plurality of lesser amounts over a period of time sufficient to elicit a response equivalent to that of a single administration of said effective amount.

4. A method of claim 1 in which the amount of interferon is administered continuously over a period of time sufficient to elicit a response equivalent to that of a single administration of said effective amount.

5. A method in accordance with claim 1, wherein said administering step comprises bringing said interferon into contact with the mucosa lining the mouth and/or throat of the mammal being treated.

6. A method of claim 1 in which the amount of interferon is from about 142.9 IU/kg/day to about $2.9 \times 10^4$ IU/kg/day of interferon.

7. A method of claim 1 in which the amount of interferon is from about 142.9 IU/kg/day to about $1.4 \times 10^4$ IU/kg/day of interferon.

8. A method of claim 1 in which the amount of interferon is from about 71.4 IU/kg/day to about $2.9 \times 10^4$ IU/kg/day of interferon.

9. A method of claim 1 wherein the interferon comprises a Type I interferon.

10. A method of claim 9 wherein the interferon is selected from the group consisting of IFN-α, IFN-β, IFN-ω, consensus IFN, and mixtures thereof.

11. A method of claim 10 wherein the IFN-α comprises recombinant IFN-α.

12. A method of claim 1 wherein the interferon comprises a Type II interferon.

13. A method of claim 1 further comprising the co-administration of other cytokines or interferon inducers.

14. A method in accordance with claim 1, wherein said pathogenic condition is other than a rhinovirus.

15. In a method for stimulating systemic host defense mechanisms against a pathogenic condition in a mammal, which method comprises administering to the mammal having such a condition a therapeutically effective amount of an interferon via oromucosal contact, the improvement wherein said amount is from about 21.4 IU/kg/day to about 2.9×10$^4$ IU/kg/day, wherein said amount is less than an amount which induces a pathological response in a mammal when administered parenterally, provided that said oromucosal administration is such that it does not involve direct action of the interferon on virally infected cells, and provided that when the condition is rhinovirus, the interferon is not administered through the mouth by multiple or continuous doses.

16. A method for treating an autoimmune, mycobacterial, neurodegenerative, parasitic, or viral condition in a mammal which method comprises administering to the mammal having such a condition a therapeutically effective amount of an interferon via oromucosal contact, said amount being from about 1500 IU/day to about 20×10$^6$ IU/day, where said amount is less than an amount which induces a pathological response in the mammal when administered parenterally.

17. The method according to claim 16, wherein the viral condition is selected from the group consisting of herpes varicella and herpes zoster.

18. The method according to claim 17, wherein the viral condition is herpes varicella.

19. The method according to claim 17, wherein the viral condition is herpes zoster.

* * * * *

UNITED STATES PATENT AND TRADEMARK OFFICE
CERTIFICATE OF CORRECTION

PATENT NO.    : 6,361,769 B1
DATED         : March 26, 2002
INVENTOR(S)   : Michael Gerard Tovey It is certified that error appears in the above-identified patent and that said Letters Patent is hereby corrected as shown below:

<u>Title page,</u>
Add the following item
-- [30] Foreign Application Priority Data
May 9, 1996  (AU)  ………………….. PN 9765 --

Signed and Sealed this

Eighth Day of October, 2002

Attest:

Attesting Officer

JAMES E. ROGAN
*Director of the United States Patent and Trademark Office*